United States Patent [19]

Esanu

[11] 4,137,316
[45] Jan. 30, 1979

[54] ANTI-DEPRESSIVE VINCAMINE PYRIDOXAL-5-PHOSPHATE

[75] Inventor: André Esanu, Paris, France

[73] Assignee: Societe d'Etudes de Produits Chimiques, Paris, France

[21] Appl. No.: 794,938

[22] Filed: May 9, 1977

[30] Foreign Application Priority Data

May 11, 1976 [GB] United Kingdom ............... 19290/76

[51] Int. Cl.² .................. A61K 31/445; C07D 519/04
[52] U.S. Cl. ........................................ 424/256; 546/24
[58] Field of Search ...................... 260/293.53, 293.55, 260/297 V, 297 P; 424/256, 267

[56] References Cited

U.S. PATENT DOCUMENTS

| 2,828,315 | 3/1958 | Wilson | 260/297 V |
| 3,891,640 | 6/1975 | Plat et al. | 260/293.53 |
| 3,925,393 | 12/1975 | Heurtaux et al. | 260/293.53 |
| 3,982,002 | 9/1976 | Montoro et al. | 260/293.53 |
| 4,021,430 | 5/1977 | Plat et al. | 260/293.53 |

FOREIGN PATENT DOCUMENTS 585226  2/1977  Switzerland ..................... 260/293.55

Primary Examiner—Henry R. Jiles
Assistant Examiner—Richard A. Schwartz
Attorney, Agent, or Firm—Eyre, Mann, Lucas & Just

[57] ABSTRACT

A new vincamine salt of therapeutic interest is disclosed. The salt is vincamine pyridoxal 5-phosphate and exhibits surprisingly greater activity than vincamine alone. A process for the preparation of the compound is also disclosed.

2 Claims, No Drawings

ANTI-DEPRESSIVE VINCAMINE PYRIDOXAL-5-PHOSPHATE

This invention relates to a new vincamine salt of therapeutic interest, to its preparation and to therapeutic compositions containing it. The new vincamine salt is vincamine pyridoxal phosphate which has the formula:

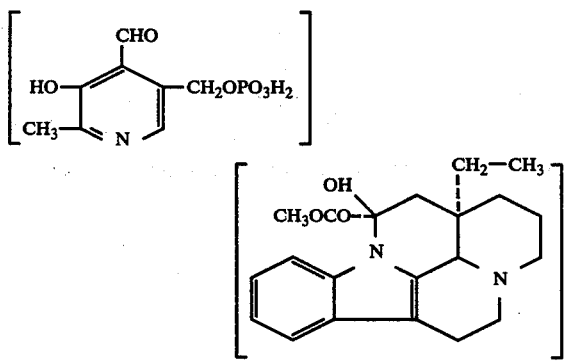

The new salt is a yellow powder, fairly soluble in water and giving a colourless solution. The compound is sparingly soluble in ethanol, insoluble in chloroform and soluble in dimethyl sulphoxide at room temperature. It has a molecular weight of 601.58 with a percentage of vincamine of 58.92% by weight. The new salt is more particularly interesting in that it has in general a better solubility than vincamine and also has a stronger therapeutic effect than vincamine. Tests have shown it to be from 4 to 10 times more active than vincamine. Moreover, the new compound also presents some anti-depressive action which is specially interesting for patients receiving vincamine treatment who suffer from depressive syndromes.

This invention accordingly provides a therapeutic composition comprising the new salt in admixture with one or more therapeutically acceptable diluents or carriers.

The new compound may be prepared according to this invention by stirring a mixture of vincamine suspended in a mixture of water and lower alkanol (50%) and pyridoxal-5-phosphate at about 105° C. The solution obtained may be lyophilized to provide vincamine pyridoxal phosphate with a high yield.

This invention is illustrated by the following example.

EXAMPLE

Into a reactor fitted with stirring and warming means there were poured 2 liters of a 50% solution of methanol in water and 141.75 g (0.4 mol) of vincamine. This mixture was stirred and warmed at 40° C. to give a suspension to which was added 106.5 g (0.4 mol) of pyridoxal-5-phosphate monohydrate. The mixture was warmed at 105° C. whilst stirring to give a clear solution from which the methanol was extracted at 35° C. under reduced pressure. After filtration of the remaining solution to remove some small impurities, the solution was lyophilized to give to 223 g of a yellow powder, melting at about 150° C. (pasty melting). Yield : 93%. Analysis showed a good correspondence with the formula $C_{29}H_{36}N_3O_9P$.

TOXICITY

The toxicity of the compound of the invention has been determined on mice. Per os value for LD 50 as 1.4 g/kg whereas I.P. was 0.380 g/kg. By comparison with vincamine, the compound of the invention appears a little bit more toxic per os but far less toxic I.P.

PHARMACOLOGY

The new compound has been submitted to various pharmacological tests.

A. Action on per-hypocapno-anemic cerebral syndrome on dogs

From this test it has been noticed that the same results could be obtained by administering by venous perfusion 0.42 mg/kg of the compound of the invention (which corresponds theorically to 0.25 mg/kg of vincamine) as by administering by the same way 1 mg/kg of vincamine. The indication is thus that for this test vincamine pyridoxal phosphate is for the same amount of vincamine 4 times more active than vincamine alone.

B. Action on a fonctional coronary insufficiency provoked by pitressine (dogs)

With this test the new salt of the invention showed a very favourable action for the correction of hemodynamic and metabolic troubles (at the dose of 1 mg/kg) whereas in the same indications, vincamine does not present any activity.

C. Action on the perturbations on the electrogenesis generated by the cerebral ischemia (rabbits)

In this test, the compound of the invention has a very good action at doses of 50 to 100 μg/kg. Some action was obtained with 1000 μg/kg of vincamine (intraveinous route). The indication is that for this test, the action of vincamine pyridoxal phosphate is at least 10 times that of vincamine.

D. Action of EEG troubles generated by an unilateral cerebral oedema (rabbits)

The new salt of the invention and vincamine were administered at various doses. The dose of 4.2 mg/kg of vincamine pyridoxal phosphate (i.e. 2.5 mg/kg of vincamine) was found to have the same effect as the administration of 10 mg/kg of vincamine base. In this test also the activity of vincamine pyridoxal phosphate appeared 4 times better than that of vincamine.

POSOLOGY-PRESENTATION

For per os use, the preferred presentation is enteric coated tablets dosed at 5 mg of vincamine pyridoxal phosphate. For injections, the form is opaque phials containing 3 mg of lyophilized product, to be dissolved in 2 ml of isotonic solution.

Posology is from 2 to 8 tablets per diem, per os, or 1 to 2 phials per diem, intravenously.

I claim:

1. The compound vincamine pyridoxal 5-phosphate having the formula

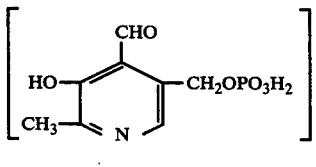

-continued
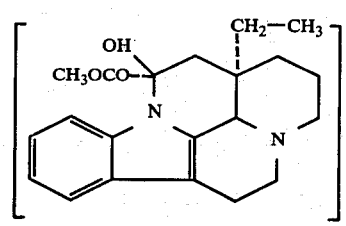
,6
2. An anti-depressive composition of matter comprising an effective anti-depressive amount of
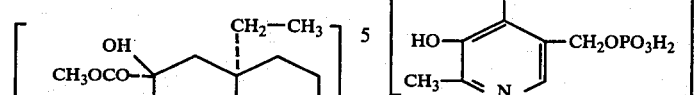
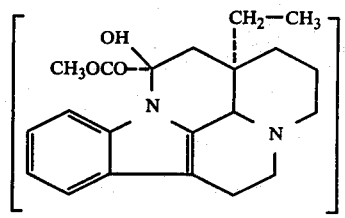
together with a therapeutically acceptable carrier therefor.
* * * * *